United States Patent [19]

Templeton et al.

[11] Patent Number: 5,124,496
[45] Date of Patent: Jun. 23, 1992

[54] PROCESS FOR DECABROMODIPHENYLALKANE PREDOMINANT PRODUCT

[75] Inventors: Mark A. Templeton, Magnolia, Ark.; Saadat Hussain, Baton Rouge, La.; Bonnie G. McKinnie, Magnolia, Ark.; Robert L. Davis, Baton Rouge, La.

[73] Assignee: Ethyl Corporation, Richmond, Va.

[21] Appl. No.: 607,822

[22] Filed: Nov. 1, 1990

[51] Int. Cl.$^5$ .................... C07C 17/12; C07C 25/18
[52] U.S. Cl. .................. 570/210; 570/206; 570/208
[58] Field of Search ............ 570/199, 206, 210, 208; 252/397, 399

[56] References Cited

U.S. PATENT DOCUMENTS

| | | | |
|---|---|---|---|
| 2,033,612 | 3/1936 | Clark et al. | 260/161 |
| 2,244,284 | 6/1941 | Britton et al. | 260/649 |
| 3,141,860 | 7/1964 | Sauer et al. | 260/33.8 |
| 3,232,959 | 2/1966 | Hahn | 260/389 |
| 3,285,965 | 11/1966 | Jenkner | 260/612 |
| 3,331,797 | 7/1967 | Kopetz et al. | 260/28.5 |
| 3,763,248 | 10/1973 | Mitchell | 260/649 |
| 3,833,674 | 9/1974 | Brackenridge | 260/649 |
| 3,959,387 | 5/1976 | Brackenridge | 260/612 |
| 3,965,197 | 6/1976 | Stepniczka | 260/623 |
| 4,287,373 | 9/1981 | Garman et al. | 568/639 |
| 4,521,633 | 6/1985 | Pedjac | 568/639 |
| 4,639,481 | 1/1987 | Giles, Jr. | 524/128 |
| 4,666,947 | 5/1987 | Brichta et al. | 521/79 |
| 4,740,629 | 4/1988 | Brackenridge et al. | 568/639 |
| 5,003,117 | 3/1991 | Hassain | 570/210 |

FOREIGN PATENT DOCUMENTS

| | | | |
|---|---|---|---|
| 708209 | 4/1965 | Canada | 568/588 |
| 0265150 | 4/1988 | European Pat. Off. | |
| 0347116 | 12/1989 | European Pat. Off. | 570/206 |
| 2950877 | 6/1981 | Fed. Rep. of Germany | 570/206 |
| 39639 | 3/1977 | Japan | 568/588 |
| 116332 | 10/1978 | Japan | 568/588 |
| 116333 | 10/1978 | Japan | 568/588 |
| 116334 | 10/1978 | Japan | 568/588 |
| 70060 | 6/1979 | Japan | |
| 981833 | 1/1965 | United Kingdom | 510/210 |
| 991067 | 5/1965 | United Kingdom | 570/210 |
| 1411524 | 10/1975 | United Kingdom | 568/588 |
| 1472383 | 5/1977 | United Kingdom | 568/588 |

OTHER PUBLICATIONS

"Flammfestmachen von Kunststoffen" by Dr. Hans Vogel, p. 49.

By Green et al. in Fire Retardants: Proceedings of 1974 International Symposium on Flammability and Fire Retardants, pp. 68-76, 1974.

By Inaba et al. in the J. Org. Chem., 49 (12), 2093-8, 1984.

By Corey et al. J. Organomet. Chem., 210(2), 149-161, 1981.

By Gassman et al. in J. Org. Chem., 47 (20), 4002-4, 1982.

Primary Examiner—Werren R. Lone
Attorney, Agent, or Firm—David E. LaRose

[57] ABSTRACT

This invention relates to a white or at least near white flame retardant product which is predominant in decarbromodiphenylalkane, and which product contains a minor amount of impurities; to a process for preparation of the flame retardant product; to a process for the removal of excess bromine from the product by use of a treatment solution and elevated temperature; and to macromolecular materials utilizing the product as a flame retardant.

24 Claims, No Drawings

PROCESS FOR DECABROMODIPHENYLALKANE PREDOMINANT PRODUCT

BACKGROUND

This invention relates to a process for preparing a flame retardant product predominant in decabromodiphenylalkane and containing less than 100 ppm excess bromine.

Polybromodiphenylalkanes, e.g. decabromodiphenylethane, are known flame retardants for use in polyolefin and polystyrenic-based formulations. On a commercial basis, the polybromodiphenylalkane would be supplied to the formulation as a product predominant in the polybromodiphenylalkane selected. The product would have a form and an impurity content which would be characteristic of the process used to produce it. If the product's physical characteristics, e.g. thermal stability, limit the formulation's processability, then the processor's desire for the product is limited at best. If the product's color is not white or at least near white, the product will be suitable for use in some formulations, however, the product's use may not be acceptable in formulations calling for a white or light color. One impurity which may affect the product's color is excess bromine.

By excess bromine is meant bromine which is in excess of the 10 bromine atoms which are attached to the carbon atoms of the aromatic rings. It is believed that at least a portion of the excess bromine is elemental bromine which may be trapped in the particle structure. Before utilizing the product in flame retardant formulations, it is highly desirable to remove as much of the excess bromine from the product as possible. Removal of excess bromine not only improves product color it also assures that formulations containing the polybromodiphenylalkane as a flame retardant will be less corrosive to the equipment used in preparing and processing the flame retardant formulations.

A well known method for removal of impurities from brominated aromatic compounds is taught by Ayres et al. U.S. Pat. No. 4,327,227. However, the removal of the excess bromine impurity from a polybrominated diphenylalkane predominant product is surprisingly much more difficult than the removal of impurities from the brominated aromatic compounds taught in Ayres et al. At highly elevated temperatures, it is believed that the excess bromine may tend to brominate the alkylene bridge linking the aromatic rings of a polybrominated diphenylalkane molecule. For example, when the diphenylalkane to be brominated is diphenylethane, an amount of dodecabromodiphenylethane may be formed at the temperature used to remove most of the excess bromine from the product.

A product containing a substantial amount of dodecabromodiphenylethane may or may not be desirable depending on the formulation in which it is used as a flame retardant. Generally, the higher the degree of bromination, the greater the degree of flame retardancy. However, for any given degree of bromination, formulations containing brominated aliphatic flame retardant products are somewhat less thermally and/or UV stable than formulations utilizing flame retardant products consisting essentially of brominated aromatic compounds.

The Invention

A process has now been discovered which provides a white or near white flame retardant product predominant in decabromodiphenylalkane and containing a minor amount of impurities. The process comprises: forming a stirrable first reaction mass by feeding molten diphenylalkane to a reaction vessel to which a bromination catalyst and bromine had been previously charged, maintaining the reaction mass at a temperature in the range of from about 0° C. to about reflux during the feeding; subsequent to the feeding, separating the decabromodiphenylalkane predominant product from the bromine and catalyst; forming a stirrable second reaction mass from the separated product and a treatment solution; and maintaining the second reaction mass for a period of time and at a temperature which is sufficient to obtain the decabromodiphenylalkane predominant product containing the minor amount of impurities.

During the preparation of the decabromodiphenylalkane predominant product, bromine is used as both a reactant and as a solvent. As a result of this process, the product usually contains an unacceptable amount of excess bromine. Until now, the method for decreasing the amount of excess bromine in the decabromodiphenylalkane predominant product has been to heat-treat the product at an elevated temperature and for an extended period of time. Under these conditions, bromination of the alkylene linkage and/or rearrangement of the decabromodiphenylalkane molecule is likely to occur. A method has now been discovered which decreases the amount of excess bromine impurity in the product in a way such that bromination of the alkylene linkage and/or rearrangement of the decabromodiphenylalkane molecule is less likely to occur.

In another embodiment, this invention provides a process for enhancing the purity of a decabromodiphenylalkane predominant product containing, at least initially, excess bromine, the process comprising forming a stirrable reaction mass, the reaction mass comprising a decabromodiphenylalkane predominant product containing excess bromine as an impurity, and a treatment solution; and maintaining the reaction mass for a period of time and at a temperature which is sufficient to obtain the enhanced decabromodiphenylalkane predominant product containing less than about 100 ppm excess bromine.

When preparing the decabromodiphenylalkane or this invention, the diphenylalkane reactant can be represented by the formula:

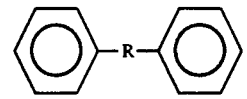

wherein R is an alkylene group containing 1 to 10 carbon atoms. Preferred R groups are methylene and ethylene which give, respectively, the preferred reactants, diphenylmethane and 1,2-diphenylethane. Exemplary of other diphenylalkanes are: 1-methyl-1,2-diphenylethane, 1,4-diphenylbutane, 1,6-diphenylhexane, 2,3-dimethyl-1,4-diphenylbutane, 2-ethyl-3-methyl-1,4-diphenylbutane, 2-methyl-1,6-diphenylhexane, 1,9-diphenylnonane and 1,10-diphenyldecane. The diphenylalkane reactant can be produced by various routes. For example, CA 97 38651d (Japanese Kokai 82/45114)

and CA 46 7084g disclose the reaction of benzene and ethylene dihalide in the presence of aluminum trichloride to yield diphenylethane. Another process for producing diphenylalkane includes the oxidative dimerization of toluene at a temperature of at least 400° C. in the presence of a metal oxide catalyst to yield diphenylethane and diphenylalkene. The latter product is then hydrogenated to remove the olefinic unsaturation.

It is not uncommon for the diphenylalkane reactant to be accompanied by various impurities. These impurities often give the final decabromodiphenylalkane product an off color. Exemplary of these color-causing impurities are benzene, toluene, ethylbenzene, diphenylmethane, the methyl and ethyl derivatives of 1,2-diphenylethane, and the like. Diminishing the impurity content can be accomplished in a conventional manner, for example, the diphenylalkane can be recrystallized.

It is highly desirable that the diphenylalkane be as pure as possible. A purity of at least about 98.0 weight percent and most preferably about 99.5 weight percent tends to provide a less colored flame retardant product than can be obtained with lower purity diphenylalkane reactant. However, this invention is not limited to the preparation of decabromodiphenylalkane predominant products from high purity reactants, as lower purity diphenylalkane may also be used.

The diphenylalkane is fed to the reaction vessel in a molten state. Thus, the diphenylalkane is at a temperature above its melting point but not so high that it experiences degradation. For diphenylethane, the melting point is about 53° C. to 55° C. and, hence, the diphenylethane is preferably fed at a temperature of from about 55° to about 80° C. The higher temperatures are preferred as the viscosity of the molten diphenylethane can be lower thus making its feed to the reaction vessel more convenient. Most preferred is a temperature within the range of from about 70° C. to about 80° C.

It is most desirable to provide a non-oxidizing atmosphere for the diphenylalkane until it is fed into the reaction vessel. Such an atmosphere can be provided by most inert gases. For example, nitrogen, argon, neon, helium, krypton, xenon, and the like. By providing the inert atmosphere, it has been found that the color characteristics of the brominated product are benefitted.

It has also been found that the bromine utilized in the process of this invention should contain 10 ppm or less organic impurities, e.g. oil, grease, carbonyl containing hydrocarbons, iron and the like, so that there is little, if any, impact on the color attributes of the product. Commercial grade bromine having such purity may be available. If such is not available, the organic impurities and water content of the bromine can be conveniently reduced by mixing together a 3 to 1 volume ratio of bromine and concentrated (94-98 percent) sulfuric acid. A two phase mix is formed which is stirred for 10-16 hours. After stirring and settling, the sulfuric acid phase, along with the impurities and water, is separated from the bromine phase. To further enhance the purity of the bromine, the recovered bromine phase can be subjected to distillation.

The bromination catalyst used in the process of this invention is preferably $AlCl_3$ and/or $AlBr_3$, although use may be made of aluminum powder, iron powder, $FeCl_3$, and $FeBr_3$, $ZrCl_4$ alone or in combination with the aluminum trihalide(s). Other bromination catalysts are suitable, provided that they have sufficient catalytic activity to provide for the extent of bromination called for under the process conditions which will be encountered. Catalytic quantities are used. Typically, the catalysts will be present in an amount within the range of about 0.1 to about 20 weight percent, based on the weight of the diphenylalkane reactant used in the process. A preferred amount is within the range of from about 8 to about 15 weight percent on the same basis, with from about 9.0 to about 11.0 weight percent being most preferred.

The bromination catalyst and bromine can be charged to the reaction vessel in any order or together. It is preferred that both be cooled or heated, as the case may be, prior to their charging so that they will form a mix which is at least near the temperature at which the reaction mass will be maintained during the diphenylalkane addition. While the foregoing is a preferred technique, it is possible, though maybe not as convenient, for the catalyst and bromine, prior to charging, to be at temperatures other than the diphenylalkane addition temperature. If, prior to charging, the catalyst and bromine temperatures are above the addition temperature, the temperature or the resultant mix in the reaction vessel can be lowered to obtain the desired addition temperature. However, care should be taken not to aspirate atmospheric moisture into the reaction vessel during such lowering. The presence of moisture in the reaction vessel is detrimental as many bromination catalysts are deactivated by contact with water.

The amount of elemental bromine ($Br_2$) charged to the reaction vessel should provide sufficient bromine to effect the degree of bromination sought and to provide an easily stirred reaction mass. Generally, from about 15 to about 30 moles of bromine per mole of diphenylalkane feed will be suitable. Preferably from about 17 to about 25 moles of bromine per mole of diphenylalkane are used. A most preferred amount is in the range of from about 18 to about 23 moles of bromine per mole of diphenylalkane. After the reaction is complete, the bromine not used in the ar-substitution will be a liquid component of the reaction mass and will continue to serve the before-mentioned purpose of providing a stirrable reaction mass.

The diphenylalkane addition generally occurs over a period of time and the addition rate is dependent upon the scale of the reaction and the ability to control the temperature and to handle hydrogen bromide evolution. On a commercial scale, the addition could involve about 1.0 to about 10.0 hours or longer.

During the diphenylalkane addition to form the first reaction mass, the reaction mass temperature is kept below about reflux, and preferably within the range of from 10° to 58° C. Since the bromination of diphenylalkane is exothermic, cooling of the reaction mass during the diphenylalkane feed ay be needed to obtain the addition temperature as required above. The heat of reaction can be removed from the first reaction mass by cooling the reaction vessel or by having the reaction mass under reflux conditions so that heat can be removed by the use of an overhead condenser. The rate of diphenylalkane addition will be dependent upon the ability of the equipment to maintain the selected addition temperature.

The bromination reaction can be accomplished at a pressure ranging from subatmospheric to superatmospheric. While the selected pressure is not critical to the invention, from a standpoint of ease of operation, it is desirable to utilize a pressure slightly above atmospheric pressure. Preferably, the pressure is above about 19 psia and most preferably, the pressure is in a range of from about 20 to about 30 psia.

It has been found that the bromination reaction is quite rapid when the diphenylalkane to be brominated is 1,2-diphenylethane. Hence, after completion of the addition of diphenylethane reactant to the reaction mass, there is little need to maintain a ride time at a temperature near or above the reaction temperature to assure substantially complete ar-bromination of the diphenylethane reactant. It may however, be desirable to maintain a post feed ride time at an elevated temperature for the ar-bromination of other diphenylalkane reactants. When a post feed ride time is desired, the reaction mass is brought to a temperature within the range of from about 55° C. to reflux after the addition of the diphenylalkane reactant is complete.

After the post feed ride time, or in the case of diphenylethane, shortly after completion of the addition of diphenylethane, e.g. after about 2 or 3 minutes, the average bromine number of the ar-brominated diphenylalkane is generally at least about 9.0. The average bromine number is defined as the average number of bromine atoms ar-substituted on each brominated diphenylalkane molecule in the product. Thus, an average bromine number of 9.0 indicates that not all of the diphenylalkane molecules in the product have been ring perbrominated, hence, the presence of the lower bromo homologs, e.g. nonabromodiphenylalkane, octabromodiphenylalkane, etc., in the product. As the average bromine number approaches 10.0, the amount of these lower bromo homologs will decrease and the amount of the decabromohomolog will increase.

After substantial completion of the addition of the diphenylalkane reactant, the first reaction mass will comprise a liquid-solid mixture. The solid comprises brominated diphenylalkane, catalyst, and other impurities. The liquid will comprise mostly bromine and impurities soluble in the bromine.

The decabromodiphenylalkane solids can be separated from the bromine reaction medium by filtration or by steam stripping the bromine. In the case of filtration, the bromine is collected as a filtrate. In the case of steam stripping, bromine is collected as a condensate. While both of these methods are effective for separation of the product from the bulk of the bromine solvent, filtration of the first reaction mass has been found to be the most preferred method since the impurities soluble in bromine are removed with the bromine in the filtrate. Even after separation from the solvent, the decabromodiphenylalkane product contains excess bromine.

The solids containing the decabromodiphenylalkane product and catalyst are then washed with an aqueous base, e.g. an aqueous solution of NaOH or $Na_2CO_3$, to neutralize and remove any HBr present and to solubilize the catalyst in the NaOH solution. A final water washing step is used to obtain a product which is predominant, i.e. 50+ weight percent, in decabromodiphenylalkane. This product is of good color and is further treated to have superior color. A preferred product is one which contains 85+ weight percent, and most preferably 90+ weight percent, decabromodiphenylalkane.

While not wishing to be bound by theory, it is believed that at least a portion of the excess bromine may be encapsulated in the decabromodiphenylalkane product or retained in the product in the form of a complex. In the encapsulated or complex form the excess bromine is difficult to remove. If an attempt is made to remove the excess bromine from the decabromodiphenylalkane product by prior art techniques, at least a portion of the bromine may react and form compounds having more than 10 bromine atoms per molecule. For example, when the decabromodiphenylalkane product is decabromodiphenylethane, a dodecabromodiphenylethane such as 1,2-dibromobis-(pentabromophenyl)-ethane may be formed.

A key feature of this invention is the removal of a substantial portion of the excess bromine from the decabromodiphenylalkane predominant product without forming detectable quantities of compounds with a bromine content greater than about 10 bromine atoms per molecule. Typically, the decabromodiphenylalkane product separated from the bromine reaction medium will contain, at least initially, more than about 100 ppm free bromine and can contain as high as about 13000 ppm excess bromine or more. As beforementioned, excess bromine in the decabromodiphenylalkane predominant product contributes a substantial color component to the flame retardant product and to formulations containing the product.

To remove a substantial portion of the excess bromine from the decabromodiphenylalkane predominant product, a stirrable second reaction mass is formed from the solids separated from the first reaction mass and a treatment solution. Optionally, the decabromodiphenylalkane predominant product may be crushed and dried before removal of the excess bromine. Whether the second reaction mass is formed before or after drying the product is not critical to this invention. However, it may be less costly to form the second reaction mass prior to drying the product separated from the first reaction mass since the product will require drying after the bromine removal step.

The treatment solution which is used to form the second reaction mass may be any organic or inorganic reagent which is compatible with the decabromodiphenylalkane product and which can be easily separated from the product after reaction with the excess bromine. Preferably the treatment solution is a basic solution and more preferably an aqueous basic solution. The basic solution may be an ammonium hydroxide solution, an alkali or alkaline earth metal hydroxide, carbonate, or sulfite or mixtures thereof. In a particularly preferred embodiment, an aqueous solution of $Na_2CO_3$ and $Na_2SO_3$ in a molar ratio of about 2:1 to about 4:1 and most preverably about 3:1 $Na_2CO_3$ to $Na_2SO_3$ is used to treat the decabromodiphenylalkane product in the second reaction mass. While a basic solution is the most preferred, other solutions may be useful in removing excess bromine. Such other solutions include amines (primary, secondary, and tertiary), sulfuric acid, hydrazine hydrate, hydrazine, sodium hypochlorite, chlorinal, $Na_2S_2O_4$, and $NaHSO_3$ and the like.

When the treatment solution is a basic solution, the concentration of the basic solution can vary over a wide range. Preferably, the basic solution has a concentration in a range of from about 2 to about 30 weight percent and most preferably in a range of from about 2 to about 10 weight percent. Enough basic solution should be utilized so as to form a stirrable reaction mass and to react with essentially all of the excess bromine in the decabromodiphenylalkane product. It is highly desirable to utilize about a 100 weight percent excess of basic solution over the stoichiometric amount needed to react with essentially all of the excess bromine.

The order of addition of reactants to the reaction vessel to form the second reaction mass is not critical.

The treatment solution may be added to a reaction vessel before, after, or concurrently with the addition of the decabromodiphenylalkane product to the reaction vessel. Optionally, the treatment solution can be added to the first reaction mass after the bromination reaction is substantially complete and before or after separation of the product from the bromine and catalyst.

Once the second reaction mass is formed, the product is maintained at a temperature for a period of time which is sufficient to form the decabromodiphenylalkane predominant product containing a minor amount of impurities. By a minor amount is meant less than about 20 weight percent based on the total amount of dried and treated product thus obtained. The excess bromine remaining in the product is preferably less than about 500 ppm and most preferably, less than about 100 ppm.

During the second reaction step, the temperature of the second reaction mass is maintained above about 150° C. Preferably, the temperature is in a range of from about 170° C. to about 400° C. and most preferably from about 180° to about 300° C. The product is maintained at this temperature for 10 minutes or longer depending on the amount of bromine removal desired. Generally, the temperature is maintained for 30 minutes to about 5 hours in order to obtain the desired product with less than about 100 ppm excess bromine.

At the temperature of the second reaction mass, the pressure in the reaction vessel will generally be above armospheric pressure. The pressure, however, is a function of the particular temperature and treatment solution used. Higher or lower pressures may be used. It is less costly and more economical, however, to utilize a pressure which at least prevents excessive loss of the treatment solution from the second reaction mass.

The decabromodiphenylalkane product of this invention may be used as a flame retardant in formulation with virtually any flammable material. The material may be macromolecular, for example, a cellulosic material or a polymer. Illustrative polymers are: Olefin polymers, cross-linked and otherwise, for example, homopolymers of ethylene, propylene, and butylene; copolymers of one or more of such alkylene monomers and any other copolymerizable monomers, for example, ethylene/propylene copolymers, ethylene/ethyl acrylate copolymers and ethylene/vinyl acetate copolymers; polymers of olefinically unsaturated monomers, for example, polystyrene, e.g. high impact polystyrene, and styrene copolymers; polyurethanes; polyamides; polyimides; polycarbonates; polyethers; acrylic resins; polyesters, especially poly(ethyleneterephthalate) and poly(butyleneterephthalate); epoxy resins; alkyls; phenolics; elastomers, for example, butadiene/styrene copolymers and butadiene/acrylonitrile copolymers; terpolymers of acrylonitrile, butadiene and styrene; natural rubber; butyl rubber, and polysiloxanes. The polymer may also be a blend of various polymers. Further, the polymer may be, where appropriate, cross-linked by chemical means or by irradiation.

The amount of product used in a formulation will be that quantity needed to obtain the flame retardancy sought. It will be apparent to those skilled in the art that for all cases no single precise value for the proportion of the product in the formulation can be given, since this proportion will vary with the particular flammable material, the presence of other additives and the degree of flame retardancy sought in any given application. Further, the proportion necessary to achieve a given flame retardancy in a particular formulation will depend upon the shape of the article into which the formulation is to be made, for example, electrical insulation, tubing and film will each behave differently. In general, however, the formulation may contain from about 5 to about 40 weight percent, preferably 10 to 30 percent, of the product when it is the only flame retardant compound in the formulation.

It is especially advantageous to use the product with an inorganic compound, especially ferric oxide, zinc oxide, zinc borate, the oxide of a Group V element, for example, bismuth, arsenic, phosphorus and especially antimony, in the formulation. Of these compounds, antimony oxides is especially preferred. If such a compound is present in the formulation, the quantity of product needed to achieve a given flame-retardancy is accordingly reduced. Generally, the product and the inorganic compound are in a weight ratio of from about 1:1 to about 7:1; and preferably of from about 2:1 to about 4:1.

Formulations containing a flame retardant system comprised of the product of this invention and the above inorganic compounds may contain up to about 40 percent by weight of the system and preferably between 20 percent and 30 percent by weight.

Any of the additives usually present in formulations, e.g. plasticizers, antioxidants, fillers, pigments, UV stabilizers, etc. can be used in formulation with the product of this invention.

Thermoplastic articles formed from formulations containing a thermoplastic polymer and a product of this invention can be produced conventionally, e.g. by injection molding, extrusion molding, compression molding, and the like.

Example 1 is not of this invention but is given as an illustration of one means for obtaining a purified diphenylalkane reactant.

EXAMPLE 1

Purification of Diphenylalkane

A 1-L beaker was charged with methanol (300 mL). Crude diphenylethane (300 g) was then added. The contents of the beaker were heated and stirred at 65° C., and the resulting clear solution was then allowed to cool slowly to room temperature. A crystalline solid was formed. The solid was filtered and washed once with 120 mL methanol and then dried. The recovery was 274.5 g (91.5%). The recrystallized material had a melting point of 50° to 54° C. which is slightly higher than the 49–50° C. for the original starting diphenylethane. The starting diphenylethane had a Y.I. of 33.2 (L=81.2, a=2.9, b=16.1) while the recrystallized diphenylethane material had a Y.I. of 2.8. (L=90.8, a=−0.4, b=1.4). The recrystallized product was 99.3 weight percent diphenylethane, 13 ppm benzene, <10 ppm ethylbenzene, and 0.29 weight percent impurities.

The next example provides an illustration of a method for the production of a decabromodiphenylalkane predominant product.

EXAMPLE 2

Preparation of Decabromodiphenylethane

A 500 mL glass-lined reactor was equipped with a mechanical stirrer, a reflux condenser, a temperature sensor, a heated addition funnel, and a caustic scrubber. The reactor was charged with bromine (400 grams, 2.5 moles) and anhydrous aluminum chloride (2.1 grams, 0.015 moles). The reactor was then cooled to about 10° C. and molten diphenylethane (DPE) (18.2 grams, 0.1 moles, 98.8 weight percent DPE) at a temperature of about 80° C. and under a nitrogen atmosphere was added through the addition funnel to the reactor contents. The addition of DPE took about 17 minutes. During the addition, the temperature of the reaction mass was held at about 10° to 17° C. and the pressure in the reaction vessel was maintained at about 5 psig. After the addition of the diphenylethane was complete, the reaction mixture was heated to about 60° C. and stirred for about 3.5 hours. Following this period, the reactor contents were cooled to about 45° C. and water (200 mL) was added. The bromine solvent was removed by distillation. The product was then filtered through a sintered glass funnel, and the solids thus collected were washed with 2-100 mL portions of water, then 100 mL of 10% aqueous HCl followed by 2-100 mL portions of water.

The following examples are not of this invention, but are provided for comparison purposes.

EXAMPLE 3

A 4,000 gallon glass-lined reactor was equipped with a mechanical stirrer, a reflux condenser, a temperature sensor, a dip pipe addition line, and a caustic scrubber. The reactor was charged with bromine (33,313 pounds, 208.4 moles) and anhydrous aluminum chloride (175 pounds, 1.31 moles). The reactor was then heated to about 54° C. and molten diphenylethane (DPE) (1,636 pounds, 8.98 moles, 99.3 weight percent DPE) was added through a dip-tube to the reactor contents. The addition of DPE took about 4 hours. During the addition, the pressure in the reaction vessel was maintained at about 5 psig and the reactor was cooled so as to maintain a temperature of about 56° C. A sample taken 14 minutes after completion of the DPE feed was 98.99 weight percent decabromodiphenylethane by gas chromatography analysis (GC) for a 91.5 percent overall yield.

After the DPE feed was complete, the reactor contents were transferred to a stripper vessel containing 900 gallons of water. The stripper vessel contents were then heated with steam until the temperature was about 98° C. and the bromine solvent was distilled from the product and condensed. Free water was allowed to drain back to the stripper vessel resulting in aqueous slurry of decabromodiphenylethane predominant product and water. After bromine removal, the stripper vessel contents were cooled and 215 gallons of 25 percent caustic (2.01 percent excess) were added. The stripper vessel contents were pumped to a slurry tank and from the slurry tank, pumped batchwise to the centrifuge where the solid decabromodiphenylethane predominant product was recovered as a wet cake. The wet cake was washed with fresh water until the centrate was at a pH of about 8.0 and the wet cake was then ground and dried in a Raymond mill dryer/grinder. Analysis of the dried product indicated about 6,000 ppm free bromine, a melting point range of about 346° to 359° C., and Hunter color values of L=83.2-84.2, Y.I.=42.0-45.6, a=2.51-3.03 and b=18.8-20.1. This dried product was heat treated in a double-cone, tumble dryer at 230° C. for 40 hours. The heat treated product had a melting point of 349° C. and Hunter color values of L=80.4, a=0.5, b=7.5 and Y.I.=17.2. GC analysis of the heat treated product indicated about 5.2 weight percent 1,2-dibromo-bis-pentabromophenylethane and 94.8 weight percent decabromodiphenylethane.

EXAMPLE 4

Following the general procedure of Example 2, a decabromodiphenylethane product was produced. The product was then oven-aged at about 200° C. for 22 hours. The product thus obtained was off-white and had a melting point of 350-356° C. The product had Hunter color values as follows:

| L = 84.7 | a = −9.95 |
|---|---|
| b = 10.12 | Y.I. = 20.9 |

The product was then further oven-aged at about 250° C. for 10 hours to give a product with the following Hunter color values:

| L = 79.82 | a = 0.69 |
|---|---|
| b = 9.62 | Y.I. = 22.5 |

EXAMPLE 5

Following the general procedure of Example 2, a decabromodiphenylethane product was produced, except that purified bromine was used. The product was then oven-aged at 210° C. for 24 hours, followed by oven-aging at 250° C. for 7 hours. The product had the following Hunter color values:

| L = 84.06 | a = 1.05 |
|---|---|
| b = 7.82 | Y.I. = 17.85 |

EXAMPLE 6

Following the general procedure of Example 5 a decabromodiphenylethane product was produced, except that the diphenylethane was added in 20 minutes to the bromine and catalyst and the reaction mass was stirred for 30 minutes at about 25° C., then for 4 hours at about 50° C. The product was then oven-aged at about 210° C. for 16 hours, followed by oven-aging at about 240° C. for 3 hours. The product had the following characteristics:

Melting point range=347-356° C.
Hunter color values:

| L = 87.53 | a = −0.53 |
|---|---|
| b = 6.59 | Y.I. = 13.72 |

Analysis of the product utilizing a gas chromatograph (GC) indicated the following distribution based on GC area percent:
Br$_9$=6.8 area percent
Br$_{10}$=93.2 area percent
Br$_{12}$=none detected.

The following examples illustrate the key features of this invention.

EXAMPLE 7

Following the general procedure of Example 2, a decabromodiphenylethane product was produced. Wet cake (100.4 grams) containing the product was then charged to a 600 mL Inconel-600 autoclave which was previously thoroughly cleaned. To this product was added 125 mL of 30 weight percent ammonium hydroxide. The autoclave was sealed and heated to about 200° C. for 1.5 hours. The pressure and temperature changes that occurred during the heating were as follows:

| Time (min.) | Temp (°C.) | Pressure (psig) |
| --- | --- | --- |
| 0 | 25.0 | 0 |
| 35 | 130.3 | 189 |
| 55 | 200.7 | 383 |
| 69 | 209.5 | 405 |
| 71 | 213.4 | 421 |
| 140 | 212.0 | 428 |

The product was then cooled and filtered through a sintered glass filter. The solids thus collected were washed with water (2-50 mL) then air dried. Analysis of the product was as follows:
Hunter color:

| L = 75.61 | a = 0.95 |
| --- | --- |
| b = 8.85 | Y.I. = 21.79 |

Free bromine: was non-detectable. The product had the following distribution:
$Br_{10}$ = 100 GC area percent
$Br_{12}$ = non-detectable

EXAMPLE 8

The general procedure of Example 7 was followed, except that the highest temperature was about 206° C., the highest pressure was about 414 psig, and the treatment time was about 30 minutes. Analysis of the product was as follows:
Hunter color:

| L = 74.46 | a = 1.13 |
| --- | --- |
| b = 8.26 | Y.I. = 20.9 |

Free bromine: was 68 ppm The product had the following distribution:
$Br_{10}$ = 99.62 GC area percent
$Br_{12}$ = 0.37 GC area percent

EXAMPLE 9

Following the general procedure of Example 2, a decabromodiphenylethane product was produced except that 50 grams (0.27 moles) of diphenylethane, 975 grams (6.1 moles) of bromine and 5.5 grams (0.04 moles) of anhydrous aluminum chloride were used. After the bromination was substantially complete, 250 mL of water were added and the bromine was distilled from the mixture. After stripping the bromine, NaOH was added to obtain a pH of about 7-8. This mixture (515.0 grams) containing the decabromodiphenylethane product was placed in a 600 mL Inconel-600 autoclave. To this was added 6.5 grams (0.077 moles) $Na_2CO_3$, 3.25 grams (0.025 moles) $Na_2SO_3$, and the product was then heated. The reaction mixture was stirred every two minutes during heating. The pressure and temperature changes that occurred during the heating were as follows:

| Time (min) | Temp °C. | Pressure (psig) |
| --- | --- | --- |
| 0 | 40 | 0 |
| 18 | 128 | 0 |
| 40 | 175 | 120 |
| 59 | 208 | 260 |
| 70 | 213 | 290 |
| 79 | 226 | 390 |
| 85 | 235 | 450 |
| 94 | 239 | 480 |
| 110 | 243 | 520 |
| 142 | 248 | 560 |
| 158 | 247 | 570 |
| 167 | 246 | 560 |
| 261 | 246 | 560 |
| 274 | 225 | 380 |
| 281 | 197 | 200 |

After the product was cooled to 60° C., it was transferred to a beaker and 30 mL of 25 weight percent NaOH was added and the mixture was stirred to mix thoroughly and then centrifuged. The solids recovered were washed with 2L of water and oven dried at about 175° C. for about 20 minutes. Analysis of the product was as follows:
Hunter color: (after jet milling to 2.5 micron average particle size)

| L = 82.5 |
| --- |
| Y.I. = 14.0 | free bromine was about 40 ppm. Product analysis utilizing a gas chromatograph indicated the following distribution:
$Br_{10}$ = 94.71 GC area %
$Br_{12}$ = 2.74 GC area %

Variations of the process of this invention are within the spirit and scope of the appended claims.

What is claimed is:

1. A process for preparing a flame retardant product predominant in decabromodiphenylalkane, the process comprising: forming a stirrable first reaction mass by feeding molten diphenylalkane to a reaction vessel to which a bromination catalyst and bromine had been previously charged; maintaining the first reaction mass at a temperature in the range of from about 0° C. to about reflux during the feeding; subsequent to the feeding, separating the decabromodiphenylalkane predominant product from the bromine and catalyst; forming a stirrable second reaction mass from the separated product and a treatment solution; and maintaining the second reaction mass for a period of time and at a temperature which is sufficient to obtain the decabromodiphenylalkane predominant product.

2. The process of claim 1 wherein the diphenylalkane reactant is 1,2-diphenylethane.

3. The process of claim 1 wherein the product comprises 90+ weight percent decarbromodiphenylalkane.

4. The process of claim 3 wherein the decabromodiphenylalkane is decabromodiphenylethane.

5. The process of claim 1 wherein the amount of bromine charged provides from about 18 to about 23 moles of bromine per mole of diphenylalkane.

6. The process of claim 2 wherein the 1,2-diphenylethane is at a temperature in the range of from about 55° C. to about 80° C. when fed to the reaction vessel.

7. The process of claim 6 wherein the 1,2 diphenylethane is fed under a nitrogen atmosphere.

8. The process of claim 1 wherein the product is separated from the bromine solvent by filtering the first reaction mass and collecting the product as a wet cake.

9. The process of claim 1 wherein the second reaction mass is maintained at a temperature in the range of from about 180° C. to about 300° C. for a period of from about 1 to about 5 hours.

10. The process of claim 1 wherein the treatment solution is comprised of an ammonium hydroxide solution.

11. The process of claim 1 wherein the treatment solution is comprised of an aqueous mixture of $Na_2CO_3$ and $Na_2SO_3$ in a molar ratio of about 3:1 of $Na_2CO_3$ to $Na_2SO_3$.

12. A process for preparing a flame retardant product predominant in decabromodiphenylethane, the process comprising: forming a stirrable first reaction mass by feeding molten 1,2-diphenylethane to a reaction vessel to which a bromination catalyst and bromine had been previously charged, the molten 1,2-diphenylethane having a purity of at least 99.5 weight percent and being maintained under a non-oxidizing atmosphere prior to the feeding, and the bromine being charged in an amount which provides from about 18 to about 23 moles of bromine per mole of 1,2-diphenylethane fed; maintaining the first reaction mass at a temperature in the range of from about 15° C. to about reflux during the feeding; separating the decabromodiphenylethane predominant product from the bromine and catalyst; forming a stirrable second reaction mass from the separated product and a treatment solution; and maintaining the second reaction mass for a period of time and at a temperature which is sufficient to obtain the decabromodiphenylethane predominant product.

13. The process of claim 12 wherein the product comprises at least 90+ weight percent decabromodiphenylethane and less than about 100 ppm excess bromine.

14. The process of claim 13 wherein the product is separated from the bromine solvent by filtering the first reaction mass and collecting the product as a wet cake.

15. The process of claim 14 wherein the treatment solution is comprised of an ammonium hydroxide solution.

16. The process of claim 15 wherein the treatment solution is comprised of an aqueous mixture of $Na_2CO_3$ and $Na_2SO_3$ in a molar ratio of about 3:1 of $Na_2CO_3$ to $Na_2SO_3$.

17. The process of claim 16 wherein the temperature of the second reaction mass is in the range of from about 180° to about 300° C.

18. An ABS formulation containing a flame retardant amount of the product produced by the process of claim 17 and with or without $Sb_2O_2$ as a flame retardant synergist being present in said formulation.

19. A HIPS formulation containing a flame retardant amount of the product produced by the process of claim 17 and with or without $Sb_2O_2$ as a flame retardant synergist being present in said formulation.

20. A process for enhancing the purity of a decabromodiphenylalkane predominant product containing, at least initially, excess bromine, the process comprising:
   a) forming a stirrable reaction mass, the reaction mass comprising a decabromodiphenylalkane predominant product containing excess bromine as an impurity, and a treatment solution; and
   b) maintaining the reaction mass for a period of time and at a temperature which is sufficient to obtain the enhanced decabromodiphenylalkane predominant product containing less than about 100 ppm excess bromine.

21. The process of claim 20 wherein the decabromodiphenylalkane predominant product contains, at least initially, more than about 100 ppm excess bromine.

22. The process of claim 20 wherein the temperature is in the range of from about 180° to about 350° C.

23. The process of claim 22 wherein the treatment solution is comprised of an ammonium hydroxide solution.

24. The process of claim 22 wherein the treatment solution is comprised of an aqueous mixture of $Na_2CO_3$ and $Na_2SO_3$ in a molar ratio of about 3:1 of $Na_2CO_3$ to $Na_2SO_3$.

* * * * *